United States Patent [19]

Walser

[11] 4,320,146

[45] Mar. 16, 1982

[54] TREATMENT OF HEPATIC AND RENAL DISORDERS WITH ORNITHINE AND ARGININE SALTS OF BRANCHED CHAIN KETO ACIDS

[75] Inventor: Mackenzie Walser, Ruxton, Md.

[73] Assignee: The Johns Hopkins University, Baltimore, Md.

[21] Appl. No.: 193,516

[22] Filed: Oct. 2, 1980

Related U.S. Application Data

[62] Division of Ser. No. 887,570, Mar. 17, 1978, Pat. No. 4,228,099.

[51] Int. Cl.$^3$ .................... A61K 31/22; A61K 31/195
[52] U.S. Cl. ...................... 424/319; 424/311
[58] Field of Search ............................ 424/311, 319

[56] References Cited

U.S. PATENT DOCUMENTS

| | | | |
|---|---|---|---|
| 3,441,650 | 4/1969 | Georges | 260/501.11 |
| 3,950,529 | 4/1976 | Fischer et al. | 424/273 |
| 4,100,293 | 7/1978 | Walser | 424/274 |

FOREIGN PATENT DOCUMENTS

| | | |
|---|---|---|
| 814483 | 6/1969 | Canada . |
| 1432756 | 2/1966 | France . |
| 827M | 4/1967 | France . |
| 2226993 | 11/1974 | France . |
| 46-3194 | 1/1971 | Japan . |
| 1034358 | 6/1966 | United Kingdom . |

OTHER PUBLICATIONS

Matsuzawa, J. Biochemistry, 75:601–609 (1974).
Chainuvati et al., Acta Hepato-Gastroenterol 24 (1977), 434–439.
Rognstad; Biochimica et Biophysica Acta 496, 249–254 (1977).
Kisfaludy, Mat. Med. Norden 29 (1977), pp. 315–325.
Molimard et al., III, Internationales Ammonich Symposium (1977), pp. 200–206.
Muting et al., Münchener Medizinische Wochenschrift (1977), pp. 1–12.

*Primary Examiner*—Allen J. Robinson
*Attorney, Agent, or Firm*—Seidel, Gonda, Goldhammer & Panitch

[57] ABSTRACT

Novel compounds are prepared by reacting ornithine or arginine with alpha ketao analogs of branched chain essential amino acids, namely valine, leucine and isoleucine. The compounds are useful either individually or as a mixture in the treatment of hepatic disorders which are characterized by hyperammonemia and portal systemic encephalopathy. Use of these compounds in treatment of renal failure also appears promising.

13 Claims, No Drawings

TREATMENT OF HEPATIC AND RENAL DISORDERS WITH ORNITHINE AND ARGININE SALTS OF BRANCHED CHAIN KETO ACIDS

STATEMENT OF GOVERNMENT INTEREST

The invention described herein was made in part in the course of work under a grant or award from the U.S. Department of Health, Education and Welfare, National Institutes of Health.

This application is a division of my co-pending application Ser. No. 887,570, filed Mar. 17, 1978, for "ORNITHINE AND ARGININE SALTS OF BRANCHED CHAIN KETO ACIDS, ETC.", now U.S. Pat. No. 4,228,099, issued Oct. 14, 1980.

BACKGROUND OF THE INVENTION

The present invention is directed to ornithine and arginine salts of keto analogs of branched chain essential amino acids, and the use of these salts particularly in the treatment of hyperammonemia.

Various hepatic disorders are characterized by hyperammonemia and portal systemic encephalopathy. The conditions are manifested clinically after ingestion of proteins by vomiting, agitation, lethargy and impaired mental and physical processes. Prior art treatment of these conditions has generally been based upon attempts to reduce the production of ammonia in the intestines and to restrict dietary protein.

Ornithine and arginine have long been known to provide protection against the toxic effects of ammonia salts. See Greenstein et al. *Archives Of Biochemistry And Biophysics* 64:342 (1956); Gullino et al. *Archives Of Biochemistry And Biophysics* 64:319 (1956); Najarian and Harper, *Proceedings Of The Society Of Experimental Biology And Medicine* 92:560 (1956); Salvatore et al., *Archives Of Biochemistry And Biophysics* 107:499 (1964); Roberge and Charbonneau, *Life Sciences* 8:369 (1969). Attempts have been made to use these compounds therapeutically in hyperammonemic patients. See Fahey, *American Journal Of Medicine* 22:860 (1957); Cachin, *La Presse Medicale* 69:1473 (1961); and Michel, *La Presse Medicale* 79:867 (1971). However, provision of ornithine or arginine per se is limited in such patients because of their decreased tolerance for nitrogen.

Individuals suffering from hyperammonemia and portal systemic encephalopathy are commonly deficient in protein owing to their intolerance of dietary protein. Therefore, nitrogen-free analogs of essential amino acids have also been used therapeutically in hyperammonemic subjects for the reduction of ammonia in the bloodstream while simultaneously promoting protein synthesis. My U.S. Pat. Nos. 4,100,293 and 4,100,160, issued July 11, 1978, disclose the use of mixtures of keto and/or hydroxy analogs of essential amino acids in the treatment of hepatic disorders. See also Maddrey et al., *Gastroenterology* 71:190 (1976); Batshaw et al., *New England Journal Of Medicine* 292:1085 (1975); and Batshaw et al., *Pediatrics* 58:227 (1976). However, the nitrogen-free analogs of essential amino acids are somewhat unpleasant tasting and have limited solubility as Ca salts.

BRIEF SUMMARY OF THE INVENTION

According to the invention, novel compounds are provided by reacting arginine or ornithine with an alpha keto analog of a branched chain essential amino acid (sometimes referred to as branched chain keto acids or branched chain essential keto acids). The resulting ornithine and arginine salts of branched chain keto acids are highly soluble in water and are reasonably pleasant tasting, particularly in contrast to arginine, ornithine or branched chain keto acids (as sodium or calcium salts) given alone.

One or more of the ornithine or arginine salts of branched chain keto acids may be administered orally or parenterally to patients suffering from hyperammonemia or portal systemic encephalopathy in order to alleviate these conditions. Preferably, such conditions are treated with a mixture of the ornithine salts of all three branched chain keto acids, namely the alpha keto analogs of valine, leucine and isoleucine.

DETAILED DESCRIPTION OF PREFERRED EMBODIMENTS

The novel compounds of the present invention are salts formed by the reaction of arginine or ornithine with alpha keto analogs of branched chain essential amino acids. The compounds may be represented simply by the following empirical formula:

$$AK.xH_2O$$

wherein A is selected from the group consisting of arginine and ornithine, K is an alpha keto analog of a branched chain essential amino acid, and x varies from zero to about one. In the case of the ornithine salts, there is no water of hydration, and hence x equals zero. Anhydrous arginine salts have not been prepared, and it is not known whether the water in the above formula is water of hydration or free or bound water due to incomplete drying of the reaction product.

The branched chain essential amino acids include valine, leucine and isoleucine, and their corresponding alpha keto analogs are alpha-ketoisovaleric acid, alpha-ketoisocaproic acid and alpha-keto-beta-methylvaleric acid. These branched chain keto acids are commercially available as calcium or sodium salts thereof. Methods of making the keto acids are also well known in the art. The free acids may be prepared from the salts by addition of excess hydrochloric acid and subsequent extraction with ether and evaporation.

Arginine (also known as guanidine aminovaleric acid or 2-amino-4-guanidovaleric acid) is a semi-essential amino acid for rats. Arginine occurs naturally in the L(+) form, and is commercially available as arginine free base, as the glutamate (see U.S. Pat. No. 2,851,482) and as the hydrochloride.

The novel arginine salts of the present invention are made by combining an aqueous solution of pure L-arginine with a stoichiometrically equivalent quantity of an aqueous solution of the desired branched chain essential keto acid. Water is then removed by evaporation. The reaction may be carried out at standard conditions of temperature and pressure, and neither the reaction method nor the water evaporation method are critical.

Ornithine (also known as 2,5-diaminovaleric acid) is a non-essential amino acid produced by the body. Ornithine occurs in two crystalline forms, namely L(+)-ornithine and DL-ornithine, but only the L form is suitable for use in the present invention. Ornithine is not generally available commercially, but may be prepared in syrup form containing a small amount of water by reacting ornithine hydrochloride with ammonium hydroxide, as detailed below.

The ornithine salts of the present invention are prepared by mixing L-ornithine syrup with the desired branched chain essential keto acid. The keto acids are also preferably used in liquid form with a small amount of water. The reaction product is then crystallized by cooling and adding ethanol.

The resulting novel compounds of the present invention which are formed by the above methods include arginine alpha-keto-isocaproate, arginine alpha-ketoisovalerate, arginine alpha-keto-beta-methylvalerate, ornithine alpha-ketoisocaproate, ornithine alpha-ketoisovalerate, and ornithine alpha-keto-beta-methylvalerate. The chemical identification of these compounds is shown below in Table 1.

The ornithine and arginine salts of alpha keto acid analogs of the branched chain essential amino acids do not exist in water because they dissociate completely, presumably into the amino acid cation and the keto acid anion. Moreover, the usual criteria of identification of organic compounds cannot be used to establish that a salt is present as opposed to a physical admixture because most such methods, such as infrared spectra, simply give the additive spectra of the components when applied to these salts.

TABLE 1

| Compound | | Chemical Analysis (wt. %) | | | | |
| --- | --- | --- | --- | --- | --- | --- |
| | | C | H | O | N | $H_2O$ |
| Arginine α-ketoisocaproate | Calc. | 47.1 | 8.1 | 29.1 | 17.5 | 4.7 |
| $C_{12}H_{24}N_4O_5 \cdot 0.838\ H_2O$ | Found | 47.1 | 8.4 | 27.0 | 17.4 | 4.8 |
| Arginine α-ketoisovalerate | Calc. | 44.1 | 7.8 | 29.4 | 18.7 | 3.2 |
| $C_{11}H_{22}N_4O_5 \cdot 0.529\ H_2O$ | Found | 44.9 | 8.1 | 29.3 | 17.5 | 3.4 |
| Arginine α-keto-β-methylvalerate | Calc. | 45.8 | 8.1 | 28.3 | 17.8 | 3.3 |
| $C_{12}H_{24}N_4O_5 \cdot 0.575\ H_2O$ | Found | 46.7 | 8.4 | 27.0 | 17.9 | 3.5 |
| Ornithine α-ketoisocaproate | Calc. | 50.4 | 8.4 | 30.5 | 10.7 | 0.0 |
| $C_{11}H_{22}N_2O_5$ | Found | 50.2 | 8.6 | 30.7 | 10.4 | Trace |
| Ornithine α-ketoisovalerate | Calc. | 48.4 | 8.1 | 32.2 | 11.3 | 0.0 |
| $C_{10}H_{20}N_2O_5$ | Found | 48.1 | 8.2 | 32.5 | 11.1 | 0.0 |
| Ornithine α-keto-β-methylvalerate | Calc. | 50.4 | 8.4 | 30.5 | 10.7 | 0.0 |
| $C_{11}H_{22}N_2O_5$ | Found | 50.2 | 8.6 | 30.8 | 10.4 | 0.0 |

Similarly, melting points could not be determined because these compounds undergo irreversible decomposition at temperatures of about 136° to 142° C. This decomposition evidently consists of the loss of a mole of water and the formation of the corresponding Schiff bases.

However, x-ray crystallographic data confirm that the compounds of the present invention are in fact organic salts, and not merely physical admixtures. For example, the x-ray crystallographic data on ornithine alpha-keto-beta-methylvalerate can be summarized as follows: the crystals are classified as space group $C222_1$. The cell dimensions are $a = 8.03 \pm 0.02$ angstrom (Å), $b = 9.69 \pm 0.02$ Å and $c = 39.52 \pm 0.05$ Å. Molecules per cell equal 8. Measured density is 1.147 grams per cubic centimeter. Volume of unit cell equal 3075 cubic angstroms. Weight of asymmetric unit equal 265.4 grams per mole (calculated as 253 grams per mole for a 1:1 salt).

The method for preparing the novel compounds of the present invention will now be described in more detail by reference to the following specific, non-limiting examples.

Preparation Of Ornithine Alpha-Ketoisocaproate

The alpha keto analog of leucine, namely alpha-ketoisocaproic acid, is first prepared from the calcium salt of the keto analog which was obtained commercially from REXIM of Paris, France. Calcium salt is suspended in water to form a slurry to which is added an excess of hydrochloric acid. The resulting clear solution is then filtered, and the filtrate is extracted with ether. The ether extract, which contains the free acid, is then removed and subjected to evaporation at reduced pressure and 30° C. Evaporation of the ether leaves behind the free keto acid, which is a liquid.

Ornithine free base is obtained by pouring a concentrated solution of commercially available ornithine hydrochloride through a large column containing a cation exchange resin, such as Dowex 50 in hydrogen form. After washing with water to remove all traces of chloride, the ornithine is then eluted by the addition of 2 N ammonium hydroxide. The eluate is then subjected to evaporation under reduced pressure at about 40° C. This results is removal of the contained free ammonia and most of the water, leaving a syrup which is the ornithine free base.

One mole of pure alpha-ketoisocaproic acid (130 grams) is added slowly with stirring to a chilled vessel containing one mole of ornithine free base (132 grams) which is obtained as a syrup. Sufficient water (about 100 ml) is added to obtain a clear solution. Sufficient absolute ethanol (about 1 liter) is added with stirring until a precipitate begins to form without redissolving on stirring. The mixture is stored over night at about 50° C. The white crystalline precipitate, which is the ornithine alpha-ketoisocaproate, is filtered and dried in air for twenty-four hours.

Preparation of Arginine Alpha-Ketoisocaproate

One mol of commercially available arginine free base (174 grams) is dissolved in about 100 ml of water and chilled. To this solution is added slowly with stirring one mol of alpha-ketoisocaproic acid (130 grams) which has been prepared according to the procedure described above. Water is then removed by evaporation under reduced pressure at about 40° C. to yield a glassy residue. Sufficient ethanol (about 250 ml) is added to dissolve this residue. The resulting solution is then evaporated to dryness under reduced pressure at 40° C. This leaves a hygroscopic white powder which is the arginine alpha-ketoisocaproate.

If desired, the compounds of the present invention may be used in other forms besides the simple organic salts. For example, upon heating the compounds give rise to the corresponding Schiff bases. In contrast to the salts per se, the Schiff bases are stable in aqueous solution. The Schiff bases would presumably be hydrolyzed in the body to give rise to arginine or ornithine and the respective branched-chain keto acids. Similarly, hydrochloride or other acid salts can be formed from the $AK \cdot xH_2O$ salts, if desired. These would of course give an acid solution when dissolved in water, as opposed to the approximately neutral solutions obtained when dissolving the AK.xH₂O salts in water.

The novel compounds of the present invention are useful in the treatment of hyperammonemia and portal systemic encephalopathy which are characteristic of various forms of hepatic (liver) disease. Beneficial effects of the novel compounds when used to treat these conditions are obtained by administering in effective dosages either individual compounds according to the invention or a mixture of the novel compounds, such as a mixture of all three arginine salts. A mixture of ornithine alpha-ketoisocaproate, ornithine alpha-ketoisovalerate and ornithine alpha-keto-beta-methylvalerate is preferred in the treatment according to the present invention.

Effective daily dosages of the novel compounds of the present invention will vary according to the weight of the patient, the severity of the condition, and other factors. An average daily dose of 30 to 40 mmoles of a compound of the present invention or of a total mixture of compounds of the present invention has been found effective. Where a mixture of compounds according to the invention is employed, it is preferred that the compounds be present in the mixture in approximately equimolar quantities.

The novel compounds of the present invention may be administered either orally or parenterally. The only prior compositions which were of much value in treating hyperammonemia were the nitrogen-free (keto and hydroxy) analogs of essential amino acids administered as sodium or calcium salts. The novel compounds of the present invention have an advantage over these prior compositions in that they are highly soluble in water (desirable for preparing aqueous parenteral solutions) and are much more pleasant tasting (desirable for oral administration). The compounds of the invention may be administered orally in dry form, such as tablets or powder.

The therapeutic efficacy for treatment of humans with the novel compounds of the present invention will now be illustrated by the following specific examples.

EXAMPLE I

A patient suffering from severe portal systemic encephalopathy was treated orally with a mixture of the three arginine salts of branched chain essential keto acids according to the present invention. Following a control period of six days, the patient received a mixture of the three salts at a total dosage of 17 mmoles per day for three consecutive days. For the following twelve consecutive days the patient was given a total dosage of 34 mmoles of the mixture per day, followed by a second control period of six days. During the treatment and the control periods immediately preceding and following the treatment, dietary nitrogen intake remained constant.

Table 2 summarizes the treatment of this patient and shows the results of a controlled nitrogen balance study during the treatment and control periods. The nitrogen balance was negative in the first control period as well as in the first three days of treatment with the smaller amounts of the mixture. However, during the next twelve days of treatment with the larger amounts of the mixture the nitrogen balance was positive. On withdrawal of therapy the nitrogen balance again became negative. As shown, the plasma ammonia content decreased throughout the therapy. In addition, substantial improvement in the clinical signs of portal systemic encephalopathy took place during the period of therapy.

TABLE 2

| Treatment | No. days | N intake, g/day Diet | N intake, g/day Drug | Plasma NH4 μM | N Balance, g/day |
|---|---|---|---|---|---|
| None | 6 | 4.7 ± 0.2 | 0.00 | 92 ± 10 | −0.9 ± 0.3 |
| Arginine ketoacids,* 17 mmol/day | 3 | 4.6 ± 0.1 | 0.95 | 84 | −0.9 ± 0.6 |
| Arginine ketoacides,** 34 mmol/day | 12 | 4.6 ± 0.2 | 1.90 | 76 ± 6 | +0.8 ± 0.3 |
| None | 6 | 4.5 ± 0.1 | 0.00 | 74 | −1.1 ± 0.3 |

*6.5 mmoles arginine α-ketoisocaproate, 5 mmoles arginine αketo-β-methylvalerate, and 5.5 mmoles arginine α-ketoisovalerate
**13 mmoles arginine α-ketoisocaproate, 10 mmoles arginine α-keto-β-methylvalerate, and 11 mmoles arginine α-ketoisovalerate

EXAMPLE II

A woman suffering from portal systemic encephalopathy was treated orally with arginine alpha-ketoisocaproate alone, and the results are summarized in Table 3. During the first five days of the control period, she was able to eat but apathetic and showed asterixis (flapping tremor) and an abnormal encephalogram. During days 6 through 9, she became almost unresponsive and intermittently semi-stuporous. Protein intake fell and nitrogen balance, which was already negative, became more so because nitrogen output did not change. Mean blood ammonia during the control period was 90±15 μM.

During the first four days of therapy (days 10–13), only minimal improvement was noted in clinical signs but blood ammonia fell somewhat (to 73 μM). Nitrogen output increased by an amount nearly equal to the nitrogen content of the drug, so that nitrogen balance did not change.

During the next seven days (days 14–20) of drug treatment, clinical signs rapidly improved, asterixis disappeared, and the abnormalities of the electroencephalogram diminished. The patient became able to eat and nitrogen balance became positive (0.1±0.5 g/day), although not statistically significantly so. Blood ammonia fell to 50 and 55 μM.

During the terminal four day control period (days 21–24), no worsening was noted.

TABLE 3

| Treatment | No. days | N intake, g/day Diet | N intake, g/day Drug | N Output, g/day | N Balance, g/day |
|---|---|---|---|---|---|
| None | 1–5 | 3.4 ±0.4 | | 4.3 ±0.3 | −0.9 ±0.4 |
| " | 6–9 | 1.1 ±0.6 | | 3.9 ±0.8 | −2.5 ±0.4 |
| Arginine alpha-ketoisocaproate, 39mmoles per day | 10–13 | 0.5 ±0.2 | 2.2 | 5.5 ±0.3 | −2.6 ±0.2 |
| Arginine alpha-ketoisocaproate, 39mmoles per day | 14–20 | 4.2 ±0.2 | 2.2 | 6.0 ±0.3 | 0.1 ±0.5 |

TABLE 3-continued

| Treatment | No. days | N intake, g/day Diet | N intake, g/day Drug | N Output, g/day | N Balance, g/day |
|---|---|---|---|---|---|
| None | 21-24 | 4.8 ±0.1 | | 4.9 ±0.5 | −0.2 ±0.5 |

EXAMPLE III

A 58 year old man with portal-systemic encephalopathy following a porto-caval shunt operation was severely symptomatic on conventional therapy, including restriction of dietary protein to 30 gm. per day, 30 ml lactulose three times a day, and sufficient laxatives to maintain two bowel movements per day. He was studied on a constant diet during a 26 day period. Following the first 8 days of control observation he received a mixture of 13 mmoles of ornithine alpha-ketoisocaproate, 10 mmoles of ornithine alpha-keto-beta-methylvalerate, and 11 mmoles of ornithine alpha-ketoisovalerate daily by mouth in three divided doses, for 10 days. An additional control period of 8 days followed.

During the first control period, his electroencephalogram was rated as grade 3 abnormal, on a scale extending from 1 (normal) to 6 (grossly abnormal). During the treatment period, his electroencephalogram was rated as grade 1.25. During the ensuing control period, it again became grade 3.

During the first control period, he exhibited pronounced asterixis (flapping tremor), ataxia, slow slurred speech, and inability to read the newspaper. During the treatment period, asterixis disappeared by the third day, ataxia improved, speech and abililty to read returned to normal or nearly normal. In the second control period, asterixis returned by the second day, gait again became ataxic, and the patient again lost interest in his surroundings.

There were no significant changes in plasma ammonia values (55 and 50 $\mu$M before treatment; 49, 49, and 61 $\mu$M during treatment; and 52 and 52 $\mu$M after treatment), despite the increase in nitrogen intake (from 4.8 gm/day, derived from the diet, to 5.8 gm/day, derived from the diet plus the nitrogen content of the medication). There were also no significant changes in plasma urea nitrogen values (13 mg/dl before treatment, 14 and 12 mg/dl during treatment, and 11 and 9 mg/dl after treatment), implying that the additional nitrogen was retained for anabolic purposes rather than being excreted.

Although applicant does not wish to be bound by any particular theory, it is believed that the salts of the present invention dissociate in body fluids to form the branched chain keto acids plus arginine and/or ornithine. The branched chain keto acids then replenish the body stores of the branched chain amino acids (leucine, valine and isoleucine) at the expense of labile nitrogenous compounds, promote protein synthesis, and inhibit excessive brain uptake of aromatic amino acids which is seen in patients with liver disease.

The beneficial effects from using arginine or ornithine alpha-ketoisocaproate alone (see Example II above) are believed to be related to a regulatory role which the essential amino acid leucine plays in protein synthesis. A recent abstract by Sherwin and Felig shows that leucine alone in a dose of approximately 15 grams per day will induce nitrogen sparing in obese subjects undergoing total starvation. Furthermore, I have found that the keto acid analog of leucine may have possible anabolic properties not shared by leucine alone.

In addition to Example II above, ornithine alpha-ketoisocaproate alone was administered to a patient suffering from severe portal-systemic encephalopathy. The patient was semi-comatose and responded dramatically to oral administration of 10 grams of ornithine alpha-ketoisocaproate given by stomach tube. The patient was awake and alert the following days but unfortunately developed peritonitis, a common complication in such individuals, and went on to die.

The mechanisms by which arginine and ornithine produce beneficial effects by virtue of their presence in the compositions of the present invention are not fully known or understood. However, it is known that ornithine is required for and is used catalytically in the urea cycle, the last step of the urea cycle being the cleavage of arginine into ornithine plus urea. It is also known that ornithine is not found in protein and therefore can be obtained only from the cleavage of dietary arginine or from arginine derived from tissue breakdown.

There is recent evidence that ornithine is destroyed by an enzyme (ornithine transaminase) almost as fast as it gains access to the interior of the mitochondrion, where it is used in the urea cycle (see J. D. McGivan et al. *Biochemistry Journal* 162:147-156 (1977)). Furthermore, the rate of transport of ornithine into the mitochondrion may be rate limiting for urea formation. Therefore, even though ornithine is a catalyst which is neither produced nor consumed by the urea cycle, it is possible that under certain circumstances excess ornithine may be required to compensate for the ornithine which is destroyed by this enzyme which is not a part of the cycle.

Recent evidence has also been obtained in the study of neonatal citrullinemia that abnormally large quantities of arginine (and presumably also of ornithine) are required to prevent hyperammonemia in this disorder. Thus, despite the still poorly understood stimulatory effect of ornithine on the urea cycle, one can conclude that a high level of arginine (as a source of ornithine) or a high level of ornithine itself will lead to a relatively higher rate of urea production for any given level of urea precursor (including ammonia) concentration of body fluids.

Aside from the above theorized mechanisms, it appears that administration of the compounds of the present invention gives synergistic effects greater than the total effects of administering either arginine or ornithine alone or administering branched chain keto acids alone. This synergistic effect may be explained from the mechanism whereby the ornithine (given as such or derived from arginine) that is destroyed by ornithine transaminase gives rise to nitrogen in the form of glutamate which then reacts with the keto acid to give rise to essential amino acids which are then used for protein synthesis. In contrast, the prior art arginine and ornithine salts of organic acids, such as the malates or alpha-ketoglutarates or citrates, are all very rapidly oxidized in the body to carbon dioxide and water. It is conjectural whether these latter organic acids alone would have any beneficial effects in the treatment of hyperammonemia.

The present invention may be embodied in other specific forms without departing from the spirit or essential attributes thereof and, accordingly, reference should be made to the appended claims, rather than to the foregoing specification as indicating the scope of the invention.

I claim:

1. A composition for promoting protein synthesis by improving nitrogen balance in subjects with liver disease comprising a carrier and an effective amount of at least one compound having the formula:

AK.$x$H$_2$O wherein A is selected from the group consisting of arginine and ornithine, K is an alpha keto analog of a branched chain essential amino acid, and x varies from zero to about one.

2. A composition according to claim 1 comprising a mixture of said compounds formed from each of the alpha keto analogs of valine, leucine and isoleucine.

3. A composition according to claim 2 comprising a mixture of arginine alpha-ketoisocaproate, arginine alpha-ketoisovalerate and arginine alpha-keto-beta-methylvalerate.

4. A composition according to claim 3 wherein said compounds are present in approximately equimolar amounts.

5. A method for promoting protein synthesis by improving nitrogen balance in subjects with liver disease which method comprises oral or parenteral administration in effective dosages to subjects suffering from this condition of a composition comprising a mixture of arginine and/or ornithine salts of alpha keto analogs of branched chain essential amino acids.

6. A method according to claim 5 wherein the mixture comprises arginine alpha-ketoisocaproate, arginine alpha-ketoisovalerate and arginine alpha-keto-beta-methylvalerate.

7. A method according to claim 6 wherein said salts are present in the composition in approximately equimolar amounts.

8. A method according to claim 7 wherein said salts are administered orally in dry form.

9. A method according to claim 7 wherein the daily dosage is approximately 30 to 40 millimoles of the total composition.

10. A method for promoting protein synthesis by improving nitrogen balance in subjects with liver disease comprising oral or parenteral administration in effective dosages to subjects suffering from this condition of at least one compound having the formula:

AK.$x$H$_2$O wherein A is selected from the group consisting of arginine and ornithine, K is an alpha keto analog of a branched chain essential amino acid, and X varies from zero to about one.

11. A method according to claim 9 wherein said compound is arginine alpha-ketoisocaproate.

12. A method according to claim 9 wherein said compound is ornithine alpha-ketoisocaproate.

13. A method for treatment of renal failure comprising oral or parenteral administration in effective dosages to subjects suffering from this condition of at least one compound having the formula:

AK.$x$H$_2$O wherein A is selected from the group consisting of arginine and ornithine, K is an alpha keto analog of a branched chain essential amino acid, and x varies from zero to about one.

* * * * *